(12) United States Patent
Truschel

(10) Patent No.: US 11,247,010 B2
(45) Date of Patent: Feb. 15, 2022

(54) IMAGING SYSTEM AND METHOD FOR CONTROL AND DIAGNOSTICS WITHIN MECHANICAL VENTILATION

(71) Applicant: KONINKLIJKE PHILIPS N.V., Eindhoven (NL)

(72) Inventor: William Anthony Truschel, Oakmont, PA (US)

(73) Assignee: Koninklijke Philips N.V., Eindhoven (NL)

(*) Notice: Subject to any disclaimer, the term of this patent is extended or adjusted under 35 U.S.C. 154(b) by 287 days.

(21) Appl. No.: 16/346,167

(22) PCT Filed: Nov. 1, 2017

(86) PCT No.: PCT/EP2017/077965
§ 371 (c)(1),
(2) Date: Apr. 30, 2019

(87) PCT Pub. No.: WO2018/083121
PCT Pub. Date: May 11, 2018

(65) Prior Publication Data
US 2020/0046924 A1    Feb. 13, 2020

Related U.S. Application Data

(60) Provisional application No. 62/415,659, filed on Nov. 1, 2016.

(51) Int. Cl.
*A61M 16/00* (2006.01)
*A61M 16/08* (2006.01)

(52) U.S. Cl.
CPC ...... *A61M 16/024* (2017.08); *A61M 16/0051* (2013.01); *A61M 16/0883* (2014.02); *A61M 2205/14* (2013.01); *A61M 2205/3303* (2013.01); *A61M 2205/3306* (2013.01); *A61M 2205/3313* (2013.01); *A61M 2205/52* (2013.01); *A61M 2230/63* (2013.01)
(Continued)

(58) Field of Classification Search
CPC .............. A61M 16/021; A61M 16/022; A61M 16/024; A61M 16/026; A61M 16/00;
(Continued)

(56) References Cited

U.S. PATENT DOCUMENTS 5,692,497 A * 12/1997 Schnitzer .......... A61M 16/0051
128/204.21
6,705,319 B1 * 3/2004 Wodicka ........... A61M 16/0488
128/200.26
(Continued)

FOREIGN PATENT DOCUMENTS

JP        2007124126 A     5/2007

*Primary Examiner* — Rachel T Sippel
*Assistant Examiner* — Kelsey E Baller
(74) *Attorney, Agent, or Firm* — Daniel H. Brean

(57) ABSTRACT

A ventilator system (10) includes a ventilator source (12), camera (14), database (16) and controller (16). A first plurality of ventilation components in a ventilation circuit (34) are coupled between the ventilator source and a patient. The camera captures images of the ventilation circuit. The database includes multi-view images of a second plurality of ventilation components pre-approved for use with the ventilator source. The controller (16) includes (i) a control module (22), (ii) a component recognition and identification module (24), (iii) a component tracking module (26) configured to track targets and to detect at least one change in tracked targets, and (iv) a ventilation compensation module (28). An operation of the ventilator source (12) is controlled with operating parameters determined as a function of at least (i) a gas composition algorithm, (ii) an output of the component recognition and identification module (24), and (iii) an output of the ventilation compensation module (28) determined as a function of an output of the component tracking module (26).

19 Claims, 8 Drawing Sheets

(58) Field of Classification Search
CPC .......... A61M 16/0051; A61M 16/2205; A61M 16/14; A61M 16/18; A61M 16/33; A61M 16/3306; A61M 16/3334; A61M 16/50; A61M 16/52; A61M 16/502; G06T 7/0012; G06T 7/62; G06T 2207/30196; G06T 2210/41
See application file for complete search history.

(56) References Cited

U.S. PATENT DOCUMENTS

| | | | |
|---|---|---|---|
| 8,122,883 B2* | 2/2012 | Banner | A61B 5/087 128/204.23 |
| 2007/0274693 A1* | 11/2007 | Farbarik | A61M 16/0069 388/806 |
| 2011/0043628 A1 | 2/2011 | Yun | |
| 2011/0138315 A1 | 6/2011 | Vandine et al. | |
| 2011/0305376 A1 | 12/2011 | Neff | |
| 2013/0255682 A1 | 10/2013 | Jafari et al. | |
| 2014/0002246 A1 | 1/2014 | Steinhauer et al. | |
| 2014/0027380 A1 | 1/2014 | Childers et al. | |
| 2015/0144130 A1* | 5/2015 | O'Donnell | A61M 16/0051 128/202.22 |
| 2015/0297903 A1* | 10/2015 | Kantor | A61M 15/009 128/200.23 |
| 2016/0030691 A1 | 2/2016 | Berry | |
| 2016/0095998 A1 | 4/2016 | Rice et al. | |
| 2017/0128304 A1* | 5/2017 | Hight | A61B 5/742 |
| 2017/0303821 A1* | 10/2017 | Hete | A61M 16/0006 |
| 2017/0368277 A1* | 12/2017 | Adametz | A61M 16/0069 |
| 2018/0286518 A1* | 10/2018 | Raju | G16H 30/40 |

* cited by examiner (A)
Connected (B)
Disconnected (A)
Straight - bend radius = ∞

(B)
Bent - bend radius < ∞

US 11,247,010 B2

IMAGING SYSTEM AND METHOD FOR CONTROL AND DIAGNOSTICS WITHIN MECHANICAL VENTILATION

CROSS-REFERENCE TO PRIOR APPLICATIONS

This application is the U.S. National Phase application under 35 U.S.C. § 371 of International Application No. PCT/EP2017/077965, filed on Nov. 1, 2017, which claims the benefit of U.S. Provisional Patent Application No. 62/415,659, filed on Nov. 1, 2016. These applications are hereby incorporated by reference herein.

The present embodiments relate generally to mechanical ventilators and more particularly, to a method incorporating an imaging system to facilitate control and monitoring systems within the ventilator.

Mechanical ventilators generate a flow and pressure of gas and measure these variables in order to provide respiratory assistance to a patient in the form of a prescription therapy. This therapy is applied through a variety of interfaces that are either invasively attached to the patient, such as an endo-tracheal tube or tracheostomy tube, or non-invasively connected, such as a nasal mask, full face mask or nasal cannula. The measurement of the pneumatic variables can be done close to the patient or within the ventilator itself distal from the patient. Often times it is advantageous to measure the variables within the ventilator distal from the patient, because this region is not exposed to any expectorate of the patient such as water, mucous and other gaseous metabolites from the patient airways. Exposure to these contaminants makes the measurements less reliable in the clinic.

When measuring ventilation properties with sensors distal from the patient, compensation must be applied to the measurements to account for losses associated with the pneumatic properties of the ventilation circuit and patient interface in between the measurement location(s) and the patient to which the therapy is applied. The rules for this compensation are often built into the ventilator device algorithms or learned through a manual calibration of the ventilation circuit and patient interface. Often, it is the responsibility of a caregiver to 'program' the ventilator device to apply the correct compensation for the ventilation circuit and patient interface. For example, the caregiver may input the tubing length, endo-tracheal tube diameter or humidification settings to the ventilator to allow the ventilator to adjust the therapy. These methods fail in various circumstances, including but not limited to, when the caregiver neglects to input the proper components or programs the ventilator with incorrect components. Other methods fail whenever the ventilator's compensation assumptions differ from reality. The manual calibration is also not fool-proof, because the ventilator controller's memory may have stored a previous calibration not relevant to the existing ventilation circuit and patient interface.

Accordingly, an improved method and apparatus for overcoming the problems in the art is desired.

According to one embodiment, a ventilator system apparatus with ventilation circuit component tracking configured to provide ventilation during a ventilation application comprises a ventilator source, a camera, a database, and a controller operatively coupled to the ventilator source, the camera, and the database. The ventilator source has an output port configured to output a ventilation gas, wherein the output port is configured to be coupled via a first plurality of ventilation components in a ventilation circuit between the ventilator source and a patient. The camera is configured to capture images of at least two or more of (i) the ventilator source, (ii) one or more component of the first plurality of ventilation components, and (iii) the patient. The database includes multiview images of at least a second plurality of ventilation components pre-approved for use with at least the ventilator source. The controller includes at least (i) a control module, (ii) a component recognition and identification module, (iii) a component tracking module configured to track targets within a plurality of real-time images captured via the camera and to detect at least one change in tracked targets, and (iv) a ventilation compensation module. The control module is configured to control an operation of the ventilator source with operating parameters determined as a function of at least (i) a gas composition algorithm, (ii) an output of the component recognition and identification module, and (iii) an output of the ventilation compensation module determined as a function of an output of the component tracking module, wherein responsive to the operating parameters, the ventilator source outputs the ventilation gas with one or more ventilation properties.

In another embodiment, the component recognition and identification module is configured to recognize or identify within a captured image, via at least template matching with the multiview images of the database, at least two or more of (i) the ventilator source, (ii) one or more component of the first plurality of ventilator components, and (iii) one or more characteristic of the patient, wherein the output of the component recognition and identification module includes data indicative of the recognized or identified at least two or more of (i) the ventilator source, (ii) one or more component of the first plurality of ventilator components, and (iii) one or more characteristic of the patient.

In another embodiment, the tracked targets include two or more of (a) the recognized or identified ventilator source, (b) the recognized or identified one or more component of the first plurality of ventilator components, (c) the recognized or identified one or more characteristic of the patient, and (d) one or more interrelationship, connection, or physical condition thereof. In addition, the component tracking module is further configured to detect at least one change in the one or more interrelationship, connection, or physical condition of the tracked targets. Furthermore, the output of the component tracking module includes data indicative of the at least one detected change in the one or more interrelationship, connection, or physical condition of the tracked targets.

The ventilator system apparatus further includes wherein the ventilation compensation module is configured to perform at least one selected from the group consisting of (i) modify at least one input to the gas composition algorithm in response to the at least one detected change in the one or more interrelationship, connection, or physical condition of the tracked targets, wherein the output of the ventilation compensation module includes data indicative of the modified at least one input to the gas composition algorithm and (ii) generate an internal alarm, wherein the control module is further configured to implement a ventilator diagnostic algorithm in response to the internal alarm. The ventilator system still further includes wherein the output of the ventilation compensation module is a direct input to the gas composition algorithm for modifying a gas density of the ventilation gas output into the ventilation circuit.

In yet another embodiment, the tracked targets include at least a ventilator hose, and wherein the at least one detected change comprises a change in bend radius of the ventilator hose. The change in bend radius of the ventilator hose includes a transition between (i) a first bend radius corresponding to the ventilator hose being straight and (ii) a second bend radius corresponding to the ventilator hose being other than straight or bent. In a further embodiment, the gas composition algorithm includes an input for friction factor, based on the bend radius, to provide compensation within the ventilation circuit in response to a change orientation of the ventilator hose.

In another embodiment, the tracked targets comprise one or more connections in the ventilation circuit between an output port of the ventilator source coupled to a hose cuff of ventilator tubing, the ventilator tubing coupled to a patient interface, and the patient interface coupled to the patient. The at least one detected change further comprises a disconnection of at least one of the one or more connections. In a further embodiment, the tracked targets comprise one or more characteristics of the patient, wherein the one or more characteristics include at least one of patient color and patient chest wall movements, further wherein the at least one detected change includes at least one of a change in patient color beyond a threshold amount and a change in patient chest wall movements beyond another threshold amount.

According to another embodiment, a method for providing ventilation to a patient using a ventilator system apparatus with ventilation circuit component tracking comprises: providing a ventilator source having an output port for outputting a ventilation gas, wherein the output port is configured to be coupled via a first plurality of ventilation components in a ventilation circuit between the ventilator source and a patient; capturing images, via a camera, of at least two or more of (i) the ventilator source, (ii) one or more of the first plurality of ventilation components, and (iii) the patient; providing a database that comprises multiview images of a second plurality of ventilation components pre-approved for use with at least the ventilator source; and controlling, via a controller, an operation of the ventilator source with operating parameters to output the ventilation gas with one or more ventilation properties, wherein the controller is operatively coupled to the ventilator source, the camera, and the database, wherein the controller includes at least (i) a control module, (ii) a component recognition and identification module, (iii) a component tracking module configured to track targets within a plurality of real-time images captured via the camera and to detect at least one change in tracked targets, and (iv) a ventilation compensation module, and further wherein the operating parameters are determined as a function of at least (i) a gas composition algorithm, (ii) an output of the component recognition and identification module, and (iii) an output of the ventilation compensation module determined as a function of an output of the component tracking module.

In one embodiment, the method further comprises analyzing, via the component recognition and identification module, at least one captured image to recognize or identify at least two or more of (i) the ventilator source, (ii) one or more component of the first plurality of ventilator components, and (iii) one or more characteristic of the patient, wherein the output of the component recognition and identification module includes data indicative of the recognized or identified at least two or more of (i) the ventilator source, (ii) one or more component of the first plurality of ventilator components, and (iii) one or more characteristic of the patient.

In another embodiment, the method further comprises tracking targets, via the component tracking module, wherein the tracked targets include at least two or more of (a) the recognized or identified ventilator source, (b) the recognized or identified one or more component of the first plurality of ventilator components, (c) the recognized or identified one or more characteristic of the patient, and (d) one or more interrelationship, connection, or physical condition thereof, and further detecting, via the component tracking module, at least one change in the one or more interrelationship, connection, or physical condition of the tracked targets, wherein the output of the component tracking module includes data indicative of the at least one detected change in the one or more interrelationship, connection, or physical condition of the tracked targets.

In yet another embodiment, the method further comprises performing, via the ventilation compensation and alarm module, in response to at least one detected change in the interrelationship, connection, or physical condition of the tracked targets, at least one selected from the group consisting of (i) modifying at least one input to the gas composition algorithm in response to the at least one detected change in the one or more interrelationship, connection, or physical condition of the tracked targets, wherein the output of the ventilation compensation module includes data indicative of the modified at least one input to the gas composition algorithm, and (ii) generating an internal alarm for implementing a ventilator diagnostic algorithm. The method further includes wherein the output of the ventilation compensation module is a direct input to the gas composition algorithm for modifying a gas density of the ventilation gas output into the ventilation circuit.

In a further embodiment, a non-transitory computer-readable medium is embodied with a computer program of instructions executable by a processor for causing the processor, when executed, to perform the method for providing ventilation to a patient with ventilation circuit component tracking.

In accordance with one aspect, a ventilator system apparatus is disclosed which solves the aforementioned problems easily and automatically with use of a real time image recognition algorithm configured to identify ventilation circuit components that are actually in use. The image recognition algorithm can combine learned object patterns and features, word recognition, bar code scans and template matching to aid the ventilator system apparatus in selecting the most accurate inputs to a ventilation gas compensation algorithm. For example, in one embodiment, the system apparatus includes a low cost camera located in the panel of the device or near the pneumatic tubing ports, wherein the camera is used to collect images for use in the image recognition algorithm. Packaged ventilation circuit items may also be held near the camera for scanning of the ventilation components and/or patient interface manufacturers' bar codes before placing a respective component into the ventilation circuit to pre-load the image recognition/ processing algorithm with the scanned components.

In accordance with another aspect, the ventilator system apparatus and method advantageously eliminates the need to manually calibrate the ventilator for a ventilation circuit and patient interface while still delivering accurate therapy to the patient with distal sensors. The system and method also advantageously allows a ventilator to universally accept a greater variety of circuit components in the ventilation circuit and patient interface while maintaining a specified accuracy.

Still further advantages and benefits will become apparent to those of ordinary skill in the art upon reading and understanding the following detailed description.

The embodiments of the present disclosure may take form in various components and arrangements of components, and in various steps and arrangements of steps.

Accordingly, the drawings are for purposes of illustrating the various embodiments and are not to be construed as limiting the embodiments. In the drawing figures, like reference numerals refer to like elements.

Figure 7:
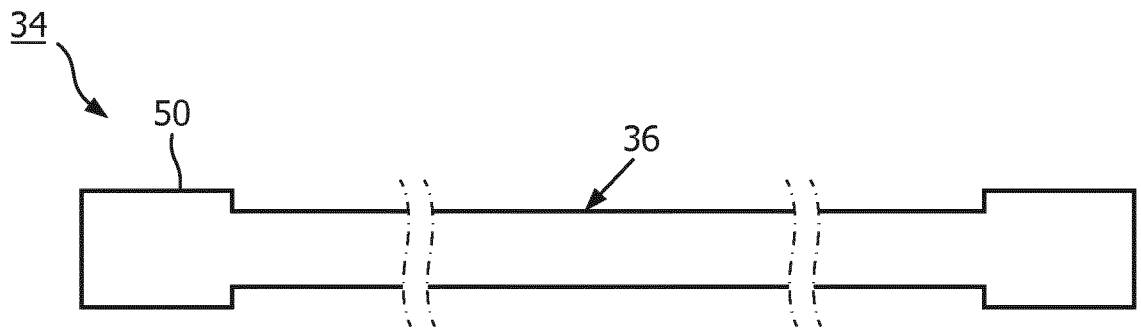
Figure 7:
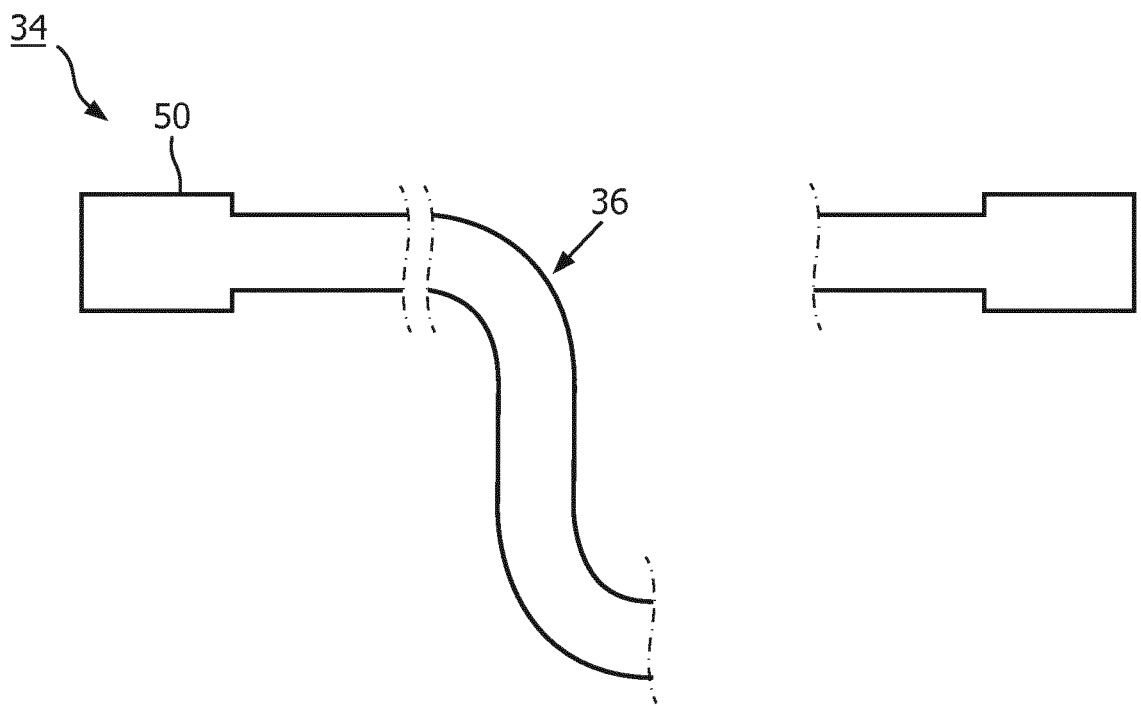
Figure 8:
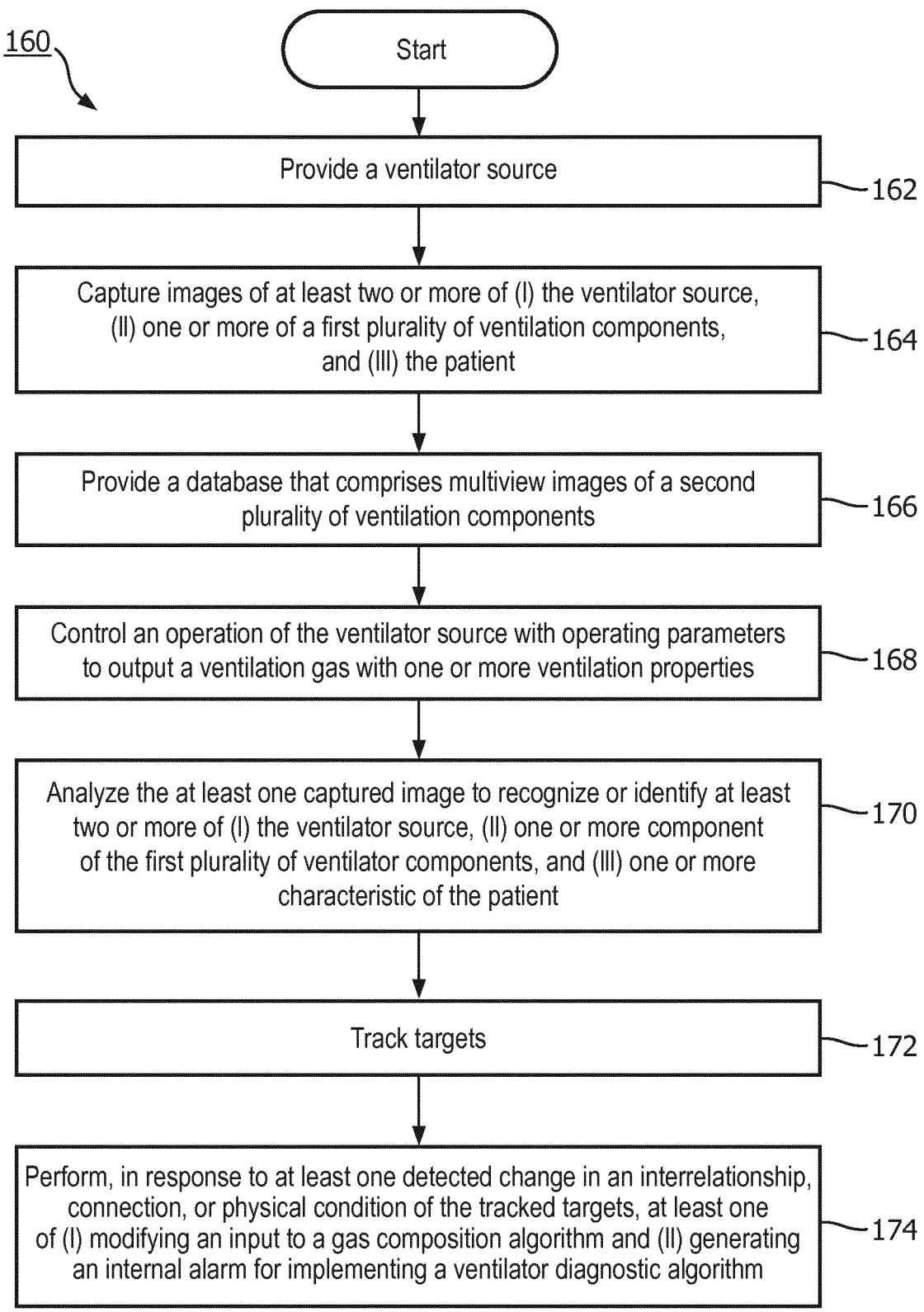

FIG. 7 is a diagram view of an example of a tracked target illustrated as having a portion thereof that is (A) straight with a bend radius equal to infinity and (B) bent or other than straight, with a bend radius less than infinity, according to another embodiment of the present disclosure; and FIG. 8 is a flow diagram view of a method for providing ventilation to a patient using a ventilator system apparatus with ventilation circuit component tracking according to another embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

The control of patient applied pressure in the mechanical ventilator is often done by controlling the pressure distally within the mechanical ventilator and applying compensation for known or calibrated components in the ventilation circuit and patient interface. Today's healthcare consumer has a large variety of circuit components from a great number of manufacturers to best fit the needs of patient when the consumer/user interfaces with the ventilator. It is a burden for the ventilator to anticipate all of these varieties and deliver accurate therapy across the spectrum. According to one embodiment, a camera placed on a medical ventilator is programmed to recognize which circuit components are placed in the ventilation circuit and patient interface. With use of image recognition software, a controller is configured to command the ventilator and make the appropriate compensation to account for the variety of components in the ventilation circuit and patient interface. As a result, the ventilator delivers accurate therapy automatically without the need for calibration or user programming of the ventilator to compensate for the ventilation circuit and patient interface.

Figure 1:
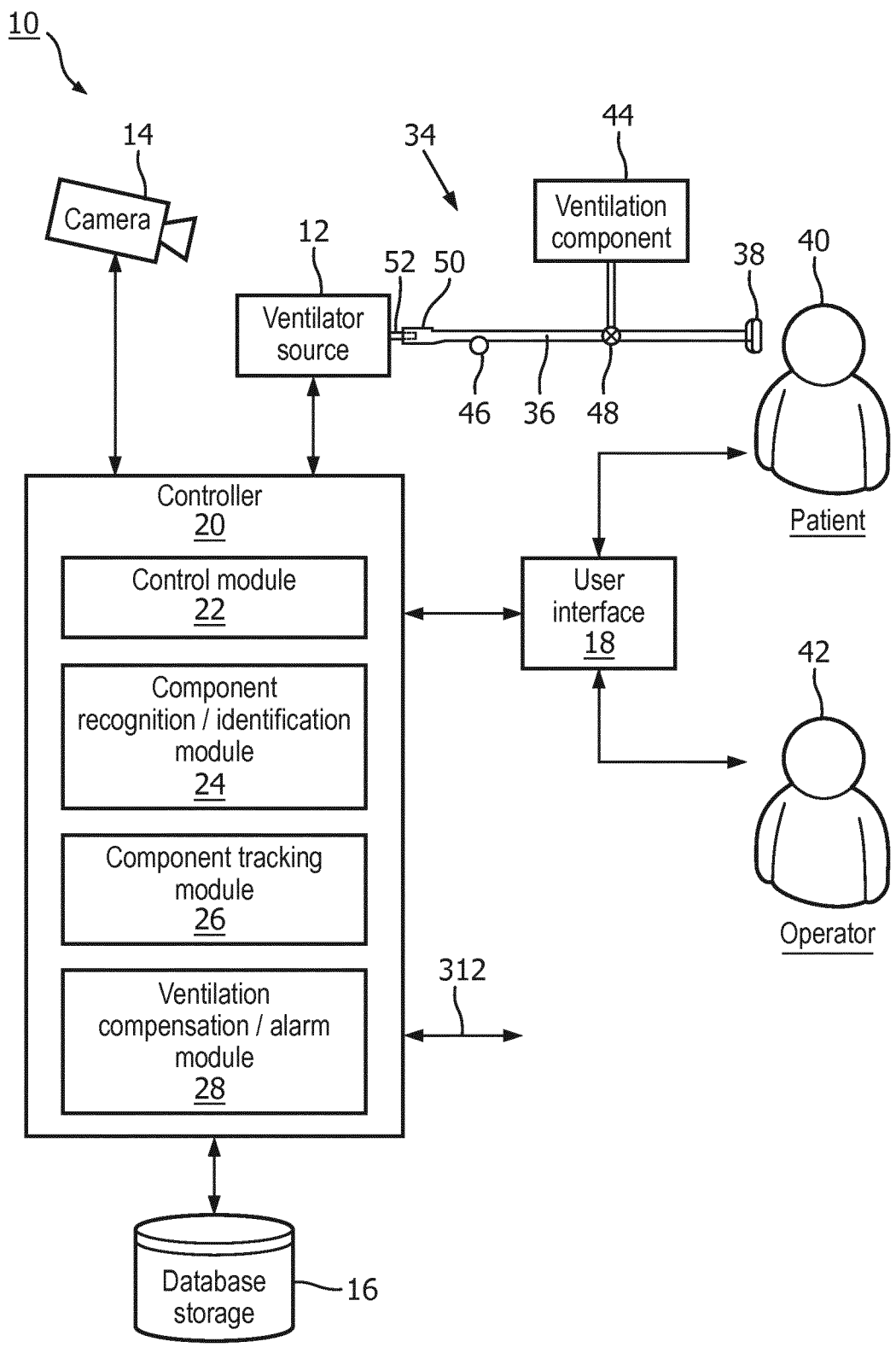
FIG. 1 is a schematic block diagram view of the ventilator system apparatus according to an embodiment of the present disclosure.

With reference now to FIG. 1, a schematic block diagram view is shown of the ventilator system apparatus 10 according to an embodiment of the present disclosure. Ventilator system apparatus 10 includes a ventilator source 12, a camera 14, a database 16 a user interface 18, and a controller 20 operatively coupled with ventilator source 12, camera 14, database 16 and user interface 18. The ventilator source 12 comprises any suitable ventilator having an output port 52 configured to output a ventilation gas. The output port 52 is configured to be coupled via a first plurality of ventilation components in a ventilation circuit 34 between the ventilator source 12 and a patient 40. The camera 14 can comprise any suitable camera configured to capture images of at least two or more of (i) the ventilator source 12, (ii) one or more component of the first plurality of ventilation components in the ventilation circuit 34, and (iii) the patient 40. In one embodiment, camera 14 comprises a video camera.

Ventilator system apparatus 10 is adapted for use with a ventilation circuit 34 that can comprise a number of various ventilation circuit components. The various ventilation circuit components include at least one or more of a ventilation hose or conduit 36 and a patient interface 38. The patient interface 38 can comprise any one of a variety of patient interfaces to be attached to a patient 40 while receiving ventilation therapy. The patient interface 38 can are either invasively attached to the patient such as an endotracheal tube or tracheostomy tube or non-invasively connected such as a nasal mask, full face mask or nasal cannula. A caregiver or operator 42 may be present during an initial setup of the ventilator system apparatus 10 and/or to assist if needed during an administration of the ventilation therapy to the patient 40. The ventilation circuit components may also include one or more ventilation component 44 (e.g., a humidifier, heater, nebulizer, etc.), one or more sensors 46 (e.g., temperature sensor, flow sensor, etc.), and one or more valves 48. In one embodiment, the ventilation hose 36 includes a hose cuff 50 at an end thereof that is configured to be coupled to an output port 52 of the ventilator source 12.

With reference still to FIG. 1, the database or storage 16 comprises electronic storage media that electronically stores information. The electronic storage media of database storage 16 can include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Database or storage 16 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Database or storage 16 may store software algorithms, information determined by controller 20, information received via user interface 18, and/or other information that enables system 10 to function properly. For example, database or storage 16 may record or store multiview images of at least a second plurality of ventilation components pre-approved for use with at least the ventilator source 12 (as discussed elsewhere herein), and/or other information. Database or storage 16 may be a separate component within system 10, or database storage 16 may be provided integrally with one or more other components of system 10 (e.g., controller 20). Furthermore, database or storage 16 may ideally be contained and maintained (i.e., updated) on a network server, shared computer, be internet based or contained within a third party data center and system 10 may access this data through a telecommunications protocol (e.g., via a wired or wireless communications connection with the third party data center).

User interface 18 is configured to provide an interface between system 10 and a user (e.g., an operator 42, patient or subject 40, a caregiver, a therapy decision-maker, etc.) through which the user can provide information to and receive information from system 10. The user interface 18 enables one or more of data, results, and/or instructions and any other communicable items, collectively referred to as "information," to be communicated between the user and system 10. An example of information that may be conveyed to patient 40 or user 42 is a report detailing trends in the patient's respiratory breathing patterns such as respiratory rate, tidal volume and applied pressures throughout a period during which the patient is receiving (respiratory) therapy. Another example of information that may be conveyed by the patient 40 and/or user 42 is an alarm or unsafe condition detected by system 10. Examples of interface devices suitable for inclusion in user interface 18 include a keypad, buttons, switches, a keyboard, knobs, levers, a display screen, a touch screen, speakers, a microphone, an indicator light, an audible alarm, and a printer. Information may be provided to patient 40 by user interface 18 in the form of auditory signals, visual signals, tactile signals, and/or other sensory signals. In one embodiment, the user interface 18 may be integrated with a removable storage interface provided by database or storage 16. In such an example, information is loaded into system 10 from removable storage (e.g., a smart card, a flash drive, a removable disk, etc.) that enables the user to customize the implementation of system 10. Other techniques for communicating information with system 10 are contemplated as user interface 18.

As noted herein above, controller 20 is operatively coupled with ventilator source 12, camera 14, database 16 and user interface 18. Controller 20 comprises one or more modules that include at least a control module 22, a component recognition and identification module 24, a component tracking module 26 configured to track targets within a plurality of real-time images captured via the camera and to detect at least one change in tracked targets, and a ventilation compensation and alarm module 28, as will be discussed further herein. In one embodiment, module 28 is configured as a ventilation compensation module, without an alarm. Furthermore, controller 20 can be configured for a wired or wireless communications connection with a remote device or network, for example, as indicated via reference numeral 32.

In one embodiment, controller 20 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given ventilator system apparatus implementation and/or application. Controller 20 can further comprise one or more of the various modules as discussed herein. Additional details regarding the controller 20 will be provided herein below with reference to the Figures. In addition, the modules 22-28 can comprise one or more of an integrated circuit, discrete analog or digital circuit components, hardware, software, firmware, or any combination thereof, for performing various functions as discussed herein, further according to the requirements of a given ventilator system apparatus implementation and/or application. Furthermore, one or more of the modules 22-28 can further comprise various combinations of one or more of the various modules.

The control module 22 of controller 20 is configured to control an operation of the ventilator source 12 with operating parameters determined as a function of at least (i) a gas composition algorithm, (ii) an output of the component recognition and identification module 24, and (iii) an output of the ventilation compensation module 28 determined as a function of an output of the component tracking module 26. In addition, the outputs of the various modules can be advantageously used to estimate ventilation circuit compliance and thus facilitate circuit compensation accuracy. The improved accuracy of circuit compliance leads to improved estimation of patient parameters, such as flow, tidal volume, and respiratory parameters such as work of breathing (WOB), muscle pressure (Pmus), pressure time product (PTP), intrinsic positive end-expiratory pressure (PEEPi). These parameters are often used to assess patient condition or are employed as an input to a closed loop ventilator control. Each component can have a cataloged compliance or the compliance can be estimated by the volume (i.e., space) of gas inside the component according to the compressibility of gas and an estimate of the size of the component. Circuit compliance is used to correct distal measurements to their respective proximal values referenced to the patient. Distal measurements are more accurate when they are corrected for losses due to the circuit, including compliance losses. In connection with circuit compliance, the phrase "circuit compensation" as generally used herein refers to the use of circuit compliance for corrective measures. In other words, the ventilator source 12 is configured to output ventilation gas with one or more ventilation properties in response to one or more operating parameters provided via the control module 22, thus providing improved patient parameter monitoring and feedback in an improved closed loop ventilator control. The improved closed loop ventilator control can also include use of input from the camera 14 (and/or data derived therefrom) as a parameter to estimate patient flow and pressure.

The component recognition and identification module 24 is configured to recognize or identify within a captured image, via at least template matching with the multiview images of the database, at least two or more of (i) the ventilator source 12, (ii) one or more component of the first plurality of ventilator components in the ventilation circuit 34 between the ventilator source 12 and the patient 40 and (iii) one or more characteristic of the patient 40. In one embodiment, the component recognition and identification module is configured to execute a number of template and/or image matching steps as follows, wherein template and/or image matching techniques are known in the art and thus only briefly discussed herein. First, the module 24 uses an objectness proposal method to list all potential component regions in the captured image. The object detection is mainly based on the richness of edges in the captured image. Around the regions having rich object edges, the module can randomly put many sliding windows as potential component regions. Then each potential component region is normalized to a fixed size and matched with all of the multi-view images of all the components in the database 16. The component having the highest matching similarity with the potential component region is assigned as being the identity of the detected region. After that, the module slightly shifts the detected region and does the same image matching to refine its location. For increasing a processing speed, the matching is based on the correlation of all the pixels of each image pair. If a powerful computing resource is available, each image will be first converted into a robust feature vector, such as deep learning based representation, and then the module performs the matching in the converted feature space. Module 24 may also implement one or more steps other than, or in addition to, those presented above for component recognition and identification. The output of the component recognition and identification module 24 includes data indicative of the recognized or identified at least two or more of (i) the ventilator source, (ii) one or more component of the first plurality of ventilator components, and (iii) one or more characteristic of the patient.

As indicated above, the component tracking module 26 is configured to track targets within a plurality of real-time images captured via the camera 14 and to detect at least one change in tracked targets. In one embodiment, the tracked targets include two or more of (a) the recognized or identified ventilator source 12, (b) the recognized or identified one or more component of the first plurality of ventilator components in the ventilation circuit 34, (c) the recognized or identified one or more characteristic of the patient 40, and (d) one or more interrelationship, connection, or physical condition thereof. Several examples of an interrelationship may include the following. With respect to the location of the patient mask, is it on the nose? Does the mask cover the mouth and nose? Is the mask connected to the stoma? Additional interrelationships are also contemplated. In one embodiment, the component tracking module 26 is configured to execute a number of steps as follows. For each recognized component, the module 26 continuously tracks its appearance over time. The tracking is done by (1) slightly shifting the target around its previous position and (2) measuring the similarity between the appearance at the shifted position and one or more of the previous appearances. The shifted position corresponding to the highest similarity will be found as the current position of the tracked target. For simplicity, the similarity is based on the correlation of image appearance directly. If powerful computing resources are available, a similarity metric based on more robust features of image appearance can be used. In the event of a sudden lighting/environment change, the tracking may fail. If this happens, then operation of module 26 ends and the recognition/identification module 24 is restarted. The component tracking module 26 is further configured to detect at least one change in the one or more interrelationship, connection, or physical condition of the tracked targets. Several examples of a change in an interrelationship may include the following. Did the patient mask separate from the patient's face to indicate a disconnect? Did the tracheostomy tube appear in the scene indicating an extubation? Other changes in interrelationships are also possible. In one embodiment, during the module's continuous tracking of each tracked target or targets, the module is continuously comparing the difference between the current appearance of the tracked targets and at least one previous appearance. If at a given moment the appearance difference becomes large (i.e., beyond a threshold amount), it is very likely that a certain change has occurred. The system can then send an alert indicative that a change has been detected. However, there may be false alarms in the event that a lighting/environment change causes the large appearance difference. This can be alleviated by comparing the color histogram of the current captured image to that of one or more previous captured image. If the histograms remain similar (e.g., within a given threshold tolerance), it indicates that the lighting/environment remains unchanged. Thus, it is safe to send an alert indicating that the change in the tracked targets has occurred. Module 26 may also implement one or more steps other than, or in addition to, those presented above for component tracking and detecting of a change in tracked targets. The output of the component tracking module 26 includes data indicative of the at least one detected change in the one or more interrelationship, connection, or physical condition of the tracked targets.

The ventilation compensation module 28 is configured to modify at least one input to the gas composition algorithm in response to the at least one detected change in the one or more interrelationship, connection, or physical condition of the tracked targets. For example, the detection of a humidifier connected in the circuit implies that the gas compensation algorithm should include water vapor. The detection of a nebulizer indicates that an aerosolized medicine would be added within the circuit and reduce the net leak of a leak compensation algorithm. In the latter instance, when nebulized flow is added to the circuit, it shows up as a negative leak. Knowing that there is negative leak introduced into the circuit enables an appropriate compensation to be applied. The output of the ventilation compensation module 28 includes data indicative of the modified at least one input to the gas composition algorithm. In one embodiment, the output of the ventilation compensation module 28 is a direct input to the gas composition algorithm for modifying a gas density of the ventilation gas output into the ventilation circuit 34. In another embodiment, the output of the ventilation compensation module 28 is an input to a leak compensation algorithm which allows the control module to synchronize with the patient along with other needs in mechanical ventilation such as flow delivery and pressure compensation familiar in mechanical ventilation. The ventilation compensation module 28 can also be configured to generate an internal alarm, wherein the control module 22 is further configured to implement a ventilator diagnostic algorithm in response to the internal alarm. For example, the detection of a lack of patient chest wall movements could indicate an obstruction or a disconnection. In another example, a patient's color could be monitored and if the patient turned blue (i.e., cyanotic), then the ventilation compensation module 28 could generate a low SpO$_2$ alarm.

Figure 2:
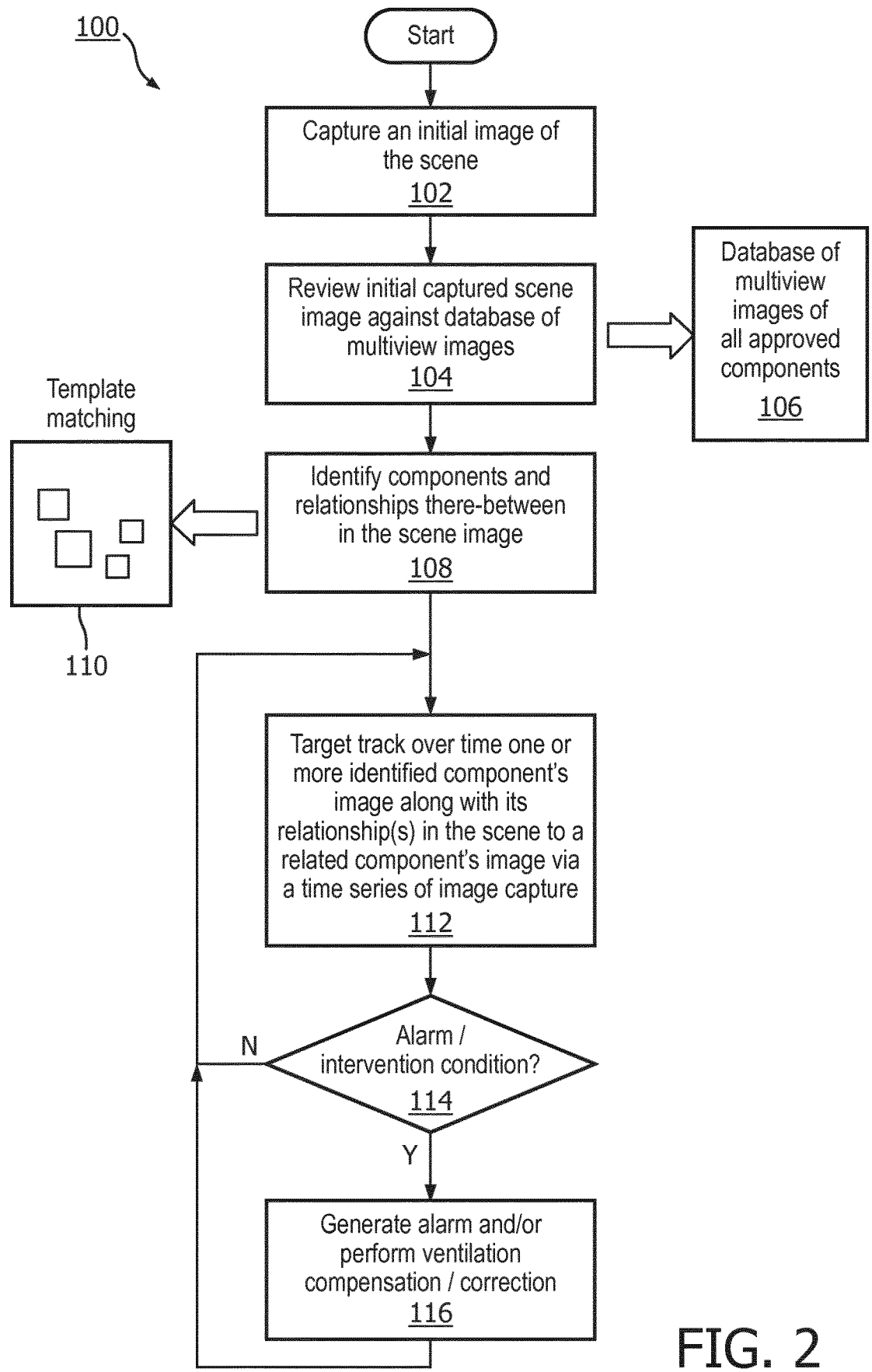
FIG. 2 is a flow diagram view of a method for providing ventilation using a ventilator system apparatus according to another embodiment of the present disclosure.

Turning now to FIG. 2, there is shown a flow diagram view 100 of a method for providing ventilation using a ventilator system apparatus according to another embodiment of the present disclosure. After setting up the ventilator system with the patient at start, an image is captured, via camera 14, of an initial scene of the ventilator system at Step 102. The image of the initial captured scene is reviewed, via the component recognition and identification module 24, against a database of multiview images at Step 104, making use of a database (e.g., database 16) of all ventilation components pre-approved for use with the ventilator source 12 (indicated at reference numeral 106). In Step 108, ventilation components and relationships there-between are identified, via the component recognition and identification module 24, in the initial scene image. In one embodiment, identification of ventilation components is accomplished via template matching or other suitable algorithms, for example, as indicated at reference numeral 110. Subsequent to recognizing or identifying the ventilator source, ventilation components and patient interface of the ventilation circuit, and the patient within the scene, the process proceeds to the next step. At Step 112, one or more of the identified component's image is target tracked, along with its relationship or relationships in the scene to one or more other components, including positions and orientations, in a time series of images captured with the camera. Target tracking is performed via component tracking module 26. At Step 114, a query is carried out regarding whether an alarm and/or intervention condition has occurred, based upon at least one detected change in an interrelationship, connection, or physical condition of one or more tracked targets. If no alarm and/or intervention condition occurs, then the process returns to the step of tracking targets (Step 112). On the other hand, if an alarm and/or intervention condition occurs, then the process proceeds to Step 116. At Step 116, the method includes generating an alarm at, for example, user interface 18 and/or performing ventilation compensation and/or correction based upon the at least one detected change in interrelationship, connection, or physical condition of the one or more tracked targets.

Figure 3:
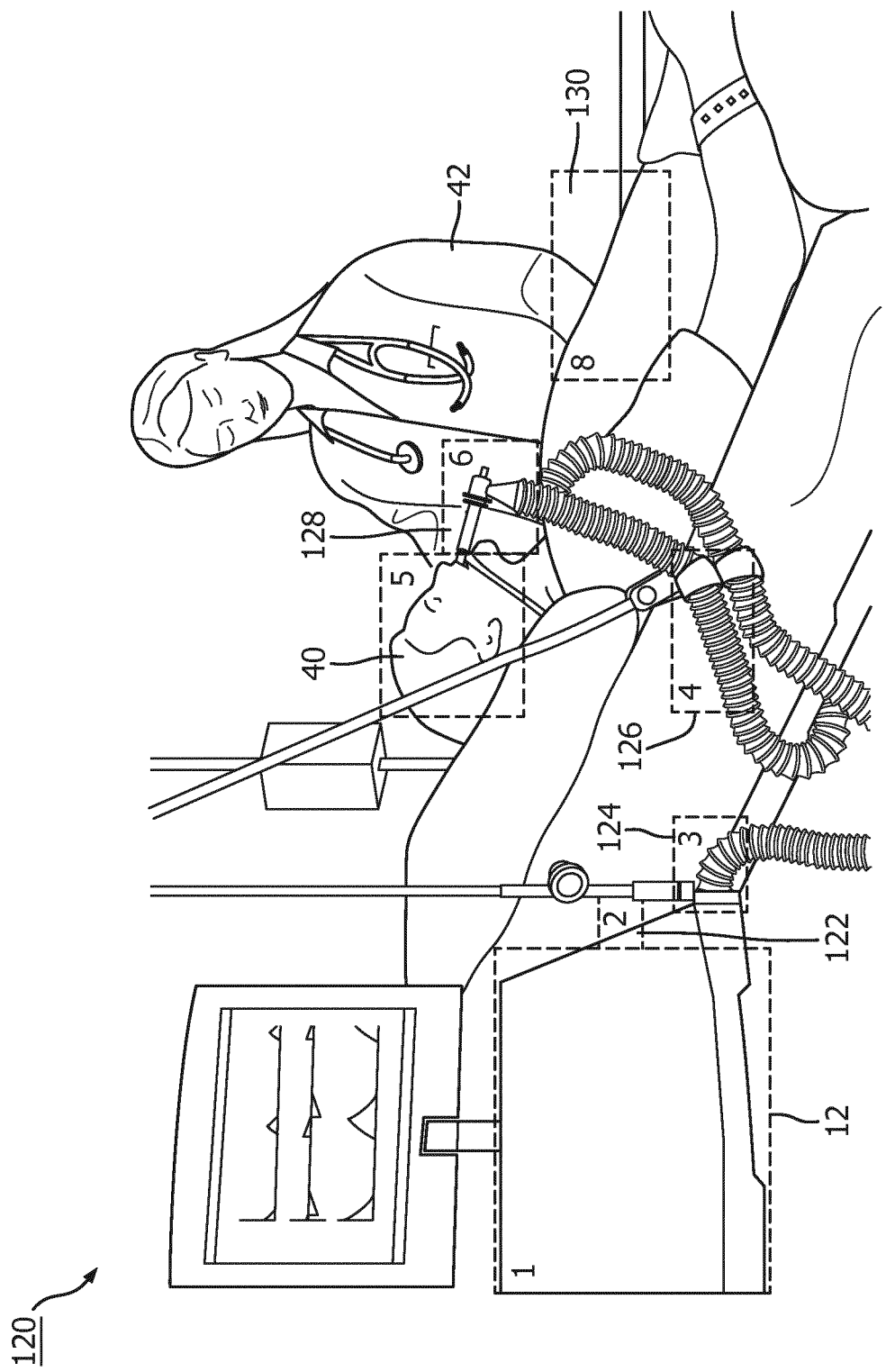
FIG. 3 is an image view of a ventilation application and template matching for component recognition and identification according to an embodiment of the present disclosure.

With reference now to FIG. 3, there is shown an image view 120 of a ventilation application and template matching for component recognition and identification according to an embodiment of the present disclosure. In the scene of the image view 120, the patient 40 is receiving ventilation therapy, as the caretaker 42 observes the patient. As discussed herein, the component recognition and identification module 24 (FIG. 1) is configured to recognize or identify within the captured image 120, via at least template matching with the multiview images of the database 16 (FIG. 1), at least two or more of (i) the ventilator source 12 (ii) one or more component of a first plurality of ventilator components, and (iii) one or more characteristic of the patient 40. In image view 120, there are included the ventilator source 12, a pressure sensor tubing connection 122 (i.e., that should be next to the ventilator source), an inhalation limb connection 124 to the ventilator source, an exhalation limb 126, patient 40, an endotracheal tube adaptor 128 (i.e., that should be next to the patient), and the patient's chest wall 130 for a respiration rate calculation. While not shown in the image view 120, an endotracheal tube, if shown, would be indicative of an unintended or accidental extubation, disconnect condition, whereby the ventilation system apparatus would issue an alarm at, for example, user interface 18. An output of the component recognition and identification module 24 includes data indicative of the recognized or identified at least two or more of (i) the ventilator source, (ii) one or more component of the first plurality of ventilator components, and (iii) one or more characteristic of the patient.

Figure 4:
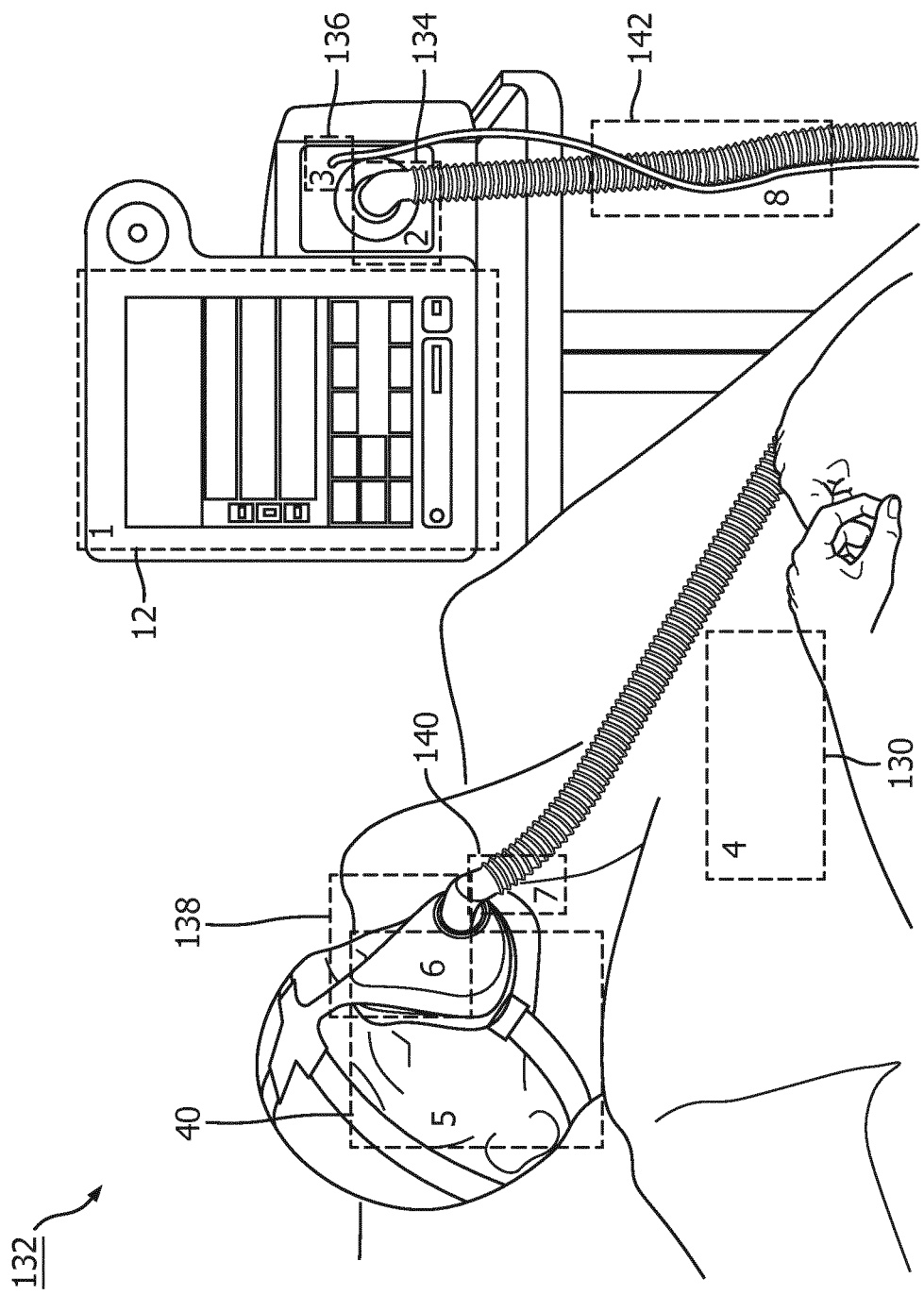
FIG. 4 is another image view of a ventilation application and template matching for component recognition and identification according to an embodiment of the present disclosure.

Similarly, with reference now to FIG. 4, there is shown another image view 132 of a ventilation application and template matching for component recognition and identification according to an embodiment of the present disclosure. In image view 132, there are included the ventilator source 12, a bacteria filter 134 that connects ventilator 12 to an inhalation limb, a pressure sense line connection 136, the patient's chest wall 130 (e.g., for a respiratory rate calculation), the patient's face 40 (e.g., for a heart rate calculation), an approved full face mask 138, a pressure sense line proximal to the patient connection 140, and corrugated 22 mm inner diameter (ID) clear tubing 142. Accordingly, in a further embodiment, the tracked targets comprise one or more characteristics of the patient, wherein the one or more characteristics include at least one of patient color and patient chest wall movements, further wherein the at least one detected change includes at least one of a change in patient color beyond a threshold amount and a change in patient chest wall movements beyond another threshold amount.

Figure 5:
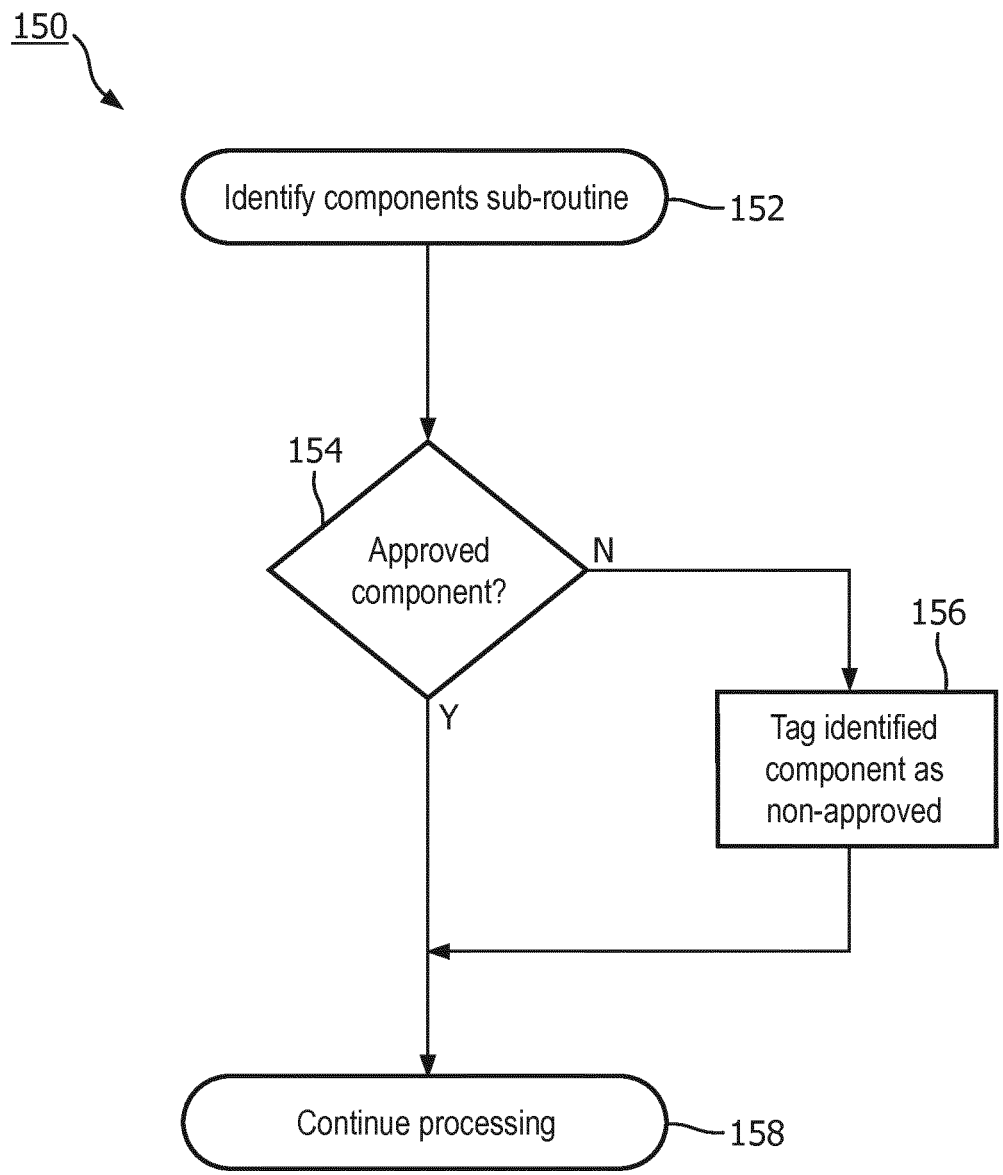
FIG. 5 is a flow diagram view of a component identification sub-routine of the ventilator system apparatus and method according to another embodiment of the present disclosure.

With reference now to FIG. 5, there is shown a flow diagram view of a component identification sub-routine 150 of the ventilator system apparatus and method according to another embodiment of the present disclosure. Step 152 is the beginning of the identify components sub-routine. A query is performed to determine whether the identified component is a component approved for use with the specific ventilator source 12 (Step 154). Responsive to the component not being approved for use with the specific ventilator source, the sub-routine proceeds to Step 156. At Step 156, the identified component is tagged as being non-approved. The tagging of identified components as non-approved can be used in later processing, for example, to carry out a default configuration setting with respect to the non-approved identified components, or some other default action according to requirements for a given ventilation therapy application. Responsive to the component being approved for use with the specific ventilator source, the sub-routine proceeds to Step 158 and returns to a main processing from which the sub-routine was called.

Figure 6:
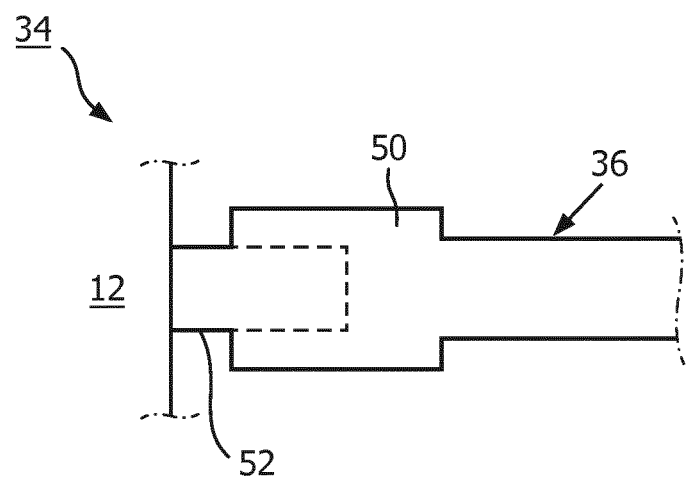
FIG. 6 is a diagram view of one example of tracked targets, shown (A) connected and (B) disconnected, according to an embodiment of the present disclosure.
Figure 6:
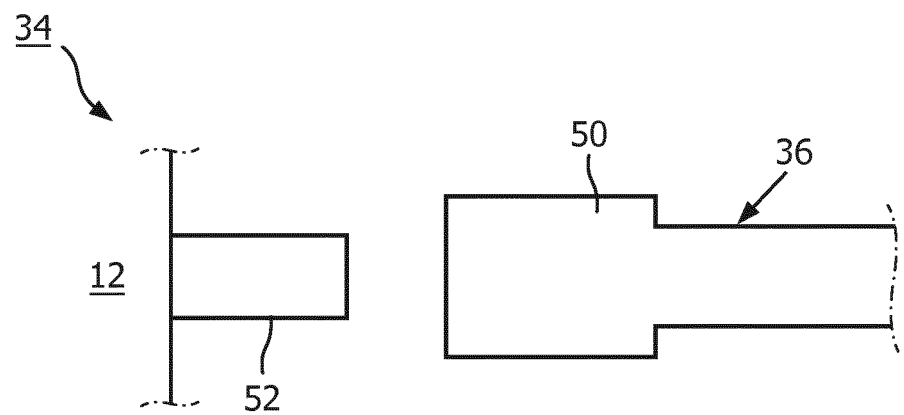

With reference now to FIG. 6, there is shown a diagram view of one example of tracked targets, shown (a) connected and (b) disconnected, according to an embodiment of the present disclosure. In this example, the tracked targets represent a connection between (i) the output port 52 of the ventilator source 12 and (ii) the cuff 50 of the ventilation hose or conduit 36 of ventilation circuit 34. The component tracking module 26 (FIG. 1) is configured to detect at least one change in the connection of the tracked targets. The output of the component tracking module includes data indicative of the at least one detected change in the connection of the tracked targets. For the illustration of FIG. 6 (A), the output of the component tracking module would comprise data indicative of a connection, whereas for the illustration of FIG. 6 (B), the output of the component tracking module would comprise data indicative of a disconnection, i.e., a change in tracked targets from a connection to a disconnection. Accordingly, in one embodiment, the tracked targets comprise one or more connections in the ventilation circuit between an output port of the ventilator source coupled to a hose cuff of ventilator tubing, the ventilator tubing coupled to a patient interface, and the patient interface coupled to the patient, and wherein the at least one detected change comprises a disconnection of at least one of the one or more connections.

Turning our attention now to FIG. 7, there is shown a diagram view of an example of a tracked target illustrated as having a portion thereof that is (a) straight with a bend radius equal to infinity and (b) bent or other than straight, with a bend radius less than infinity, according to another embodiment of the present disclosure. In this example, the tracked targets represent a physical condition of a select portion of the ventilation hose or conduit 36 of ventilation circuit 34, e.g., between two cuffs 50 at opposite ends thereof. The component tracking module 26 (FIG. 1) is configured to detect at least one change in the physical condition of the tracked targets. The output of the component tracking module includes data indicative of the at least one detected change in the physical condition of the tracked targets. For the illustration of FIG. 7 (A), the output of the component tracking module would comprise data indicative of a straight condition (i.e., bend radius=∞), whereas for the illustration of FIG. 7 (B), the output of the component tracking module would comprise data indicative of a bent condition, i.e., a change in tracked targets from straight to bent. The change is tracked targets could also include bent to straight, etc.

Accordingly, in one embodiment, the tracked targets include at least a ventilator hose 36, and wherein the at least one detected change comprises a change in bend radius of the ventilator hose 36. The change in bend radius of the ventilator hose 36 includes a transition between (i) a first bend radius corresponding to the ventilator hose being straight (FIG. 7 (A)) and (ii) a second bend radius corresponding to the ventilator hose being other than straight or bent (FIG. 7 (B)). The detected change in bend radius of the ventilator hose can include from straight to bent or from bent to straight, etc. In addition, the gas composition algorithm can further include an input for friction factor, based on the bend radius, to provide compensation within the ventilation circuit in response to the change in orientation of the ventilator hose.

According to another embodiment, a method 160, shown in FIG. 8, for providing ventilation to a patient using a ventilator system apparatus with ventilation circuit component tracking includes providing, at step 162, a ventilator source having an output port for outputting a ventilation gas. The output port is configured to be coupled via a first plurality of ventilation components in a ventilation circuit between the ventilator source and a patient. The method further includes capturing images, at step 164, via a camera, of at least two or more of (i) the ventilator source, (ii) one or more of the first plurality of ventilation components, and (iii) the patient; providing, at step 166, a database that comprises multiview images of a second plurality of ventilation components pre-approved for use with at least the ventilator source; and controlling, at step 168, via a controller, an operation of the ventilator source with operating parameters to output the ventilation gas with one or more ventilation properties, wherein the controller is operatively coupled to the ventilator source, the camera, and the database.

In implementing the method, the controller includes at least (i) a control module, (ii) a component recognition and identification module, (iii) a component tracking module configured to track targets within a plurality of real-time images captured via the camera and to detect at least one change in tracked targets, and (iv) a ventilation compensation module. The operating parameters are determined as a function of at least (i) a gas composition algorithm, (ii) an output of the component recognition and identification module, and (iii) an output of the ventilation compensation module determined as a function of an output of the component tracking module.

The method further comprises analyzing, at step 170, via the component recognition and identification module, at least one captured image to recognize or identify at least two or more of (i) the ventilator source, (ii) one or more component of the first plurality of ventilator components, and (iii) one or more characteristic of the patient. The output of the component recognition and identification module includes data indicative of the recognized or identified at least two or more of (i) the ventilator source, (ii) one or more component of the first plurality of ventilator components, and (iii) one or more characteristic of the patient.

The method further comprises tracking targets, at step 172, via the component tracking module, wherein the tracked targets include at least two or more of (a) the recognized or identified ventilator source, (b) the recognized or identified one or more component of the first plurality of ventilator components, (c) the recognized or identified one or more characteristic of the patient, and (d) one or more interrelationship, connection, or physical condition thereof. In addition, the method further includes detecting, via the component tracking module, at least one change in the one or more interrelationship, connection, or physical condition of the tracked targets. The output of the component tracking module includes data indicative of the at least one detected change in the one or more interrelationship, connection, or physical condition of the tracked targets.

Still further, the method comprises performing, at step 174, via the ventilation compensation and alarm module, in response to at least one detected change in the interrelationship, connection, or physical condition of the tracked targets, at least one selected from the group consisting of (i) modifying at least one input to the gas composition algorithm in response to the at least one detected change in the one or more interrelationship, connection, or physical condition of the tracked targets, and (ii) generating an internal alarm for implementing a ventilator diagnostic algorithm. In one embodiment, the output of the ventilation compensation module includes data indicative of the modified at least one input to the gas composition algorithm. In another embodiment, the output of the ventilation compensation module is a direct input to the gas composition algorithm for modifying a gas density of the ventilation gas output into the ventilation circuit.

In a further embodiment, the tracked targets include at least a ventilator hose, and wherein the at least one detected change comprises a change in bend radius of the ventilator hose. The change in bend radius of the ventilator hose includes a transition between (i) a first bend radius corresponding to the ventilator hose being straight and (ii) a second bend radius corresponding to the ventilator hose being other than straight or bent. In another embodiment, the gas composition algorithm further includes an input for friction factor compensation within the ventilation circuit in response to the detected change in the bend radius of the ventilator hose.

According to yet another embodiment, the method includes wherein the tracked targets comprise (i) one or more connections in the ventilation circuit between an output port of the ventilator source coupled to a hose cuff of ventilator tubing, the ventilator tubing coupled to a patient interface, and the patient interface coupled to the patient. In addition, the detected changes comprises a disconnection of at least one of the one or more connections, or (ii) one or more characteristics of the patient. The one or more characteristics can include at least one of patient color and patient chest wall movements. In addition, the at least one detected change can include at least one of a change in patient color beyond a threshold amount and a change in patient chest wall movements beyond another threshold amount.

It is understood that the modules described herein may also be computer program modules which are rendered in a non-transitory computer-readable medium. In other words, another embodiment of the present disclosure comprises a non-transitory computer-readable medium embodied with a computer program of instructions executable by a processor, for causing the processor, when executed, to perform the method for providing ventilation to a patient with ventilation circuit component tracking, as discussed herein.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in sleep apnea device applications. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A ventilator system apparatus with ventilation circuit component tracking configured to provide ventilation during a ventilation application, the apparatus comprising:
a ventilator source having an output port configured to output a ventilation gas, wherein the output port is configured to be coupled via a first plurality of ventilation components in a ventilation circuit between the ventilator source and a patient;
a camera configured to capture images of at least two or more of (i) the ventilator source, (ii) one or more component of the first plurality of ventilation components, and (iii) the patient;
a database of multiview images of at least a second plurality of ventilation components pre-approved for use with at least the ventilator source; and
a controller operatively coupled to the ventilator source, the camera, and the database, wherein the controller includes at least (i) a control module, (ii) a component recognition and identification module, (iii) a component tracking module configured to track targets within a plurality of real-time images captured via the camera and to detect at least one change in tracked targets, and (iv) a ventilation compensation module,
wherein the control module is configured to control an operation of the ventilator source with operating parameters determined as a function of at least (i) a gas composition algorithm, (ii) an output of the component recognition and identification module, and (iii) an output of the ventilation compensation module determined as a function of an output of the component tracking module, wherein responsive to the operating parameters, the ventilator source outputs the ventilation gas with one or more ventilation properties, and
wherein the tracked targets include at least a ventilator hose, and wherein the at least one detected change comprises a change in bend radius of the ventilator hose.

2. The ventilator system apparatus of claim 1, wherein the component recognition and identification module is configured to recognize or identify within a captured image, via at least template matching with the multiview images of the database, at least two or more of (i) the ventilator source, (ii) one or more component of the first plurality of ventilator components, and (iii) one or more characteristic of the patient, wherein the output of the component recognition and identification module includes data indicative of the recognized or identified at least two or more of (i) the ventilator source, (ii) one or more component of the first plurality of ventilator components, and (iii) one or more characteristic of the patient.

3. The ventilator system apparatus of claim 2, wherein the tracked targets include two or more of (a) the recognized or identified ventilator source, (b) the recognized or identified one or more component of the first plurality of ventilator components, (c) the recognized or identified one or more characteristic of the patient, and (d) one or more interrelationship, connection, or physical condition thereof, the component tracking module further being configured to detect at least one change in the one or more interrelationship, connection, or physical condition of the tracked targets, wherein the output of the component tracking module includes data indicative of the at least one detected change in the one or more interrelationship, connection, or physical condition of the tracked targets.

4. The ventilator system apparatus of claim 3, wherein the ventilation compensation module is configured to perform at least one selected from the group consisting of (i) modify at least one input to the gas composition algorithm in response to the at least one detected change in the one or more interrelationship, connection, or physical condition of the tracked targets, wherein the output of the ventilation compensation module includes data indicative of the modified at least one input to the gas composition algorithm and (ii) generate an internal alarm, wherein the control module is further configured to implement a ventilator diagnostic algorithm in response to the internal alarm.

5. The ventilator system apparatus of claim 1, wherein the change in bend radius of the ventilator hose includes a transition between (i) a first bend radius corresponding to the ventilator hose being straight and (ii) a second bend radius corresponding to the ventilator hose being other than straight or bent.

6. The ventilator system apparatus of claim 1, wherein the tracked targets comprise one or more connections in the ventilation circuit between the output port of the ventilator source coupled to a hose cuff of ventilator tubing, the ventilator tubing coupled to a patient interface, and the patient interface coupled to the patient, and wherein the at least one detected change comprises a disconnection of at least one of the one or more connections.

7. The ventilator system apparatus of claim 1, wherein the tracked targets comprise one or more characteristics of the patient, wherein the one or more characteristics include at least one of patient color and patient chest wall movements, further wherein the at least one detected change includes at least one of a change in patient color beyond a threshold amount and a change in patient chest wall movements beyond another threshold amount.

8. A method for providing ventilation to a patient using a ventilator system apparatus with ventilation circuit component tracking, the method comprising:
    providing a ventilator source having an output port for outputting a ventilation gas, wherein the output port is configured to be coupled via a first plurality of ventilation components in a ventilation circuit between the ventilator source and a patient;
    capturing images, via a camera, of at least two or more of (i) the ventilator source, (ii) one or more of the first plurality of ventilation components, and (iii) the patient;
    providing a database that comprises multiview images of a second plurality of ventilation components pre-approved for use with at least the ventilator source; and
    controlling, via a controller, an operation of the ventilator source with operating parameters to output the ventilation gas with one or more ventilation properties, wherein the controller is operatively coupled to the ventilator source, the camera, and the database, wherein the controller includes at least (i) a control module, (ii) a component recognition and identification module, (iii) a component tracking module configured to track targets within a plurality of real-time images captured via the camera and to detect at least one change in tracked targets, and (iv) a ventilation compensation module, and further wherein the operating parameters are determined as a function of at least (i) a gas composition algorithm, (ii) an output of the component recognition and identification module, and (iii) an output of the ventilation compensation module determined as a function of an output of the component tracking module;
    wherein the tracked targets include at least a ventilator hose, and wherein the at least one detected change comprises a change in bend radius of the ventilator hose.

9. The method of claim 8, further comprising analyzing, via the component recognition and identification module, at least one captured image to recognize or identify at least two or more of (i) the ventilator source, (ii) one or more component of the first plurality of ventilator components, and (iii) one or more characteristic of the patient, wherein the output of the component recognition and identification module includes data indicative of the recognized or identified at least two or more of (i) the ventilator source, (ii) one or more component of the first plurality of ventilator components, and (iii) one or more characteristic of the patient.

10. The method of claim 9, further comprising tracking targets, via the component tracking module, wherein the tracked targets include at least two or more of (a) the recognized or identified ventilator source, (b) the recognized or identified one or more component of the first plurality of ventilator components, (c) the recognized or identified one or more characteristic of the patient, and (d) one or more interrelationship, connection, or physical condition thereof, and further detecting, via the component tracking module, at least one change in the one or more interrelationship, connection, or physical condition of the tracked targets, wherein the output of the component tracking module includes data indicative of the at least one detected change in the one or more interrelationship, connection, or physical condition of the tracked targets.

11. The method of claim 10, further comprising performing, via the ventilation compensation, in response to at least one detected change in the interrelationship, connection, or physical condition of the tracked targets, at least one selected from the group consisting of (i) modifying at least one input to the gas composition algorithm in response to the at least one detected change in the one or more interrelationship, connection, or physical condition of the tracked targets, wherein the output of the ventilation compensation module includes data indicative of the modified at least one input to the gas composition algorithm, and (ii) generating an internal alarm for implementing a ventilator diagnostic algorithm.

12. The method of claim 11, wherein the output of the ventilation compensation module is a direct input to the gas composition algorithm for modifying a gas density of the ventilation gas output into the ventilation circuit.

13. The method of claim 8, wherein the change in bend radius of the ventilator hose includes a transition between (i) a first bend radius corresponding to the ventilator hose being straight and (ii) a second bend radius corresponding to the ventilator hose being other than straight or bent.

14. A method for providing ventilation to a patient using a ventilator system apparatus with ventilation circuit component tracking, the method comprising:
    providing a ventilation gas using a ventilator source having an output port configured to be coupled to ventilation components in a ventilation circuit between the ventilator source and a patient;
    obtaining images, via a camera, of targets comprising two or more of (i) the ventilator source, (ii) one or more of the ventilation components, and (iii) the patient;
    tracking, using a controller, the targets within the images and detecting a change in the targets, wherein the targets include at least a ventilator hose, and wherein the change comprises a change in bend radius of the ventilator hose;
    modifying, via the controller, gas composition of the ventilation gas in response to a detected change in interrelationship, connection, or physical condition of the targets; and
    outputting, using the ventilation source, the ventilation gas with the modified gas composition.

15. The method of claim 14, wherein the change in bend radius of the ventilator hose includes a transition between (i) a first bend radius corresponding to the ventilator hose being straight and (ii) a second bend radius corresponding to the ventilator hose being other than straight or bent.

16. The method of claim 14, wherein the targets comprise one or more of a nebulizer and a humidifier.

17. The method of claim 16, wherein the modifying the gas composition of the ventilation gas comprises changing one or more of gas density of the ventilation gas and pressure of the ventilation gas for delivery to the patient.

18. The method of claim 14, wherein:
    the targets include one or more pre-approved ventilation components; and
    the tracking comprises identifying one or more targets is not a pre-approved ventilation component.

19. The method of claim 14, comprising displaying the modified gas composition to a user.

\* \* \* \* \*